(12) United States Patent
Kakinoki (10) Patent No.: US 11,273,297 B2
(45) Date of Patent: Mar. 15, 2022

(54) MEDICAL DEVICE

(71) Applicant: TERUMO KABUSHIKI KAISHA, Tokyo (JP)

(72) Inventor: Toshihiko Kakinoki, Oyama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/560,163

(22) PCT Filed: Mar. 23, 2018

(86) PCT No.: PCT/JP2018/011872
§ 371 (c)(1),
(2) Date: Sep. 4, 2019

(87) PCT Pub. No.: WO2018/174273
PCT Pub. Date: Sep. 27, 2018

(65) Prior Publication Data
US 2020/0179672 A1 Jun. 11, 2020

Related U.S. Application Data (63) Continuation of application No. PCT/JP2018/011872, filed on Mar. 23, 2018.

(30) Foreign Application Priority Data

Mar. 24, 2017 (JP) .............................. JP2017-058832

(51) Int. Cl.
*A61M 39/26* (2006.01)
*A61M 39/10* (2006.01)
(Continued)

(52) U.S. Cl.
CPC ...... *A61M 39/1011* (2013.01); *A61M 39/221* (2013.01); *A61M 39/26* (2013.01);
(Continued)

(58) Field of Classification Search
CPC ........ A61M 39/1011; A61M 2039/267; A61M 2039/268; A61M 2039/1066;
(Continued)

(56) References Cited

U.S. PATENT DOCUMENTS

| 5,085,645 A | 2/1992 | Purdy et al. |
| 5,694,686 A * | 12/1997 | Lopez ..................... A61M 5/14 29/890.126 |

(Continued)

FOREIGN PATENT DOCUMENTS

| CN | 1240340 A | 1/2000 |
| CN | 103987423 A | 8/2014 |

(Continued)

OTHER PUBLICATIONS

International Search Report (PCT/ISA/210) dated May 29, 2018, by the Japan Patent Office as the International Searching Authority for International Application No. PCT/JP2018/011872.

(Continued)

*Primary Examiner* — Nathan R Price
*Assistant Examiner* — Courtney B Fredrickson
(74) *Attorney, Agent, or Firm* — Buchanan Ingersoll & Rooney PC (57) ABSTRACT

A medical device includes a connector portion. The connector portion includes an inner cylinder connectable to another medical device having an elastic valve, a valve body against which the elastic valve is pressed from a distal end side due to connection of the inner cylinder and another medical device, and an outer cylinder disposed radially outside the inner cylinder, and the connector portion is configured to provide fluid communication between the connector portion and another medical device by moving the inner cylinder in an axial direction with respect to the outer cylinder in a state where the inner cylinder is connected with another medical (Continued)

device. The connector portion further includes an anchor that suppresses movement of the valve body with respect to the inner cylinder toward a proximal end.

15 Claims, 8 Drawing Sheets

(51) Int. Cl.
*A61M 39/22* (2006.01)
*A61M 5/14* (2006.01)
*A61M 5/31* (2006.01)

(52) U.S. Cl.
CPC ............. *A61M 5/1413* (2013.01); *A61M 5/31* (2013.01); *A61M 2039/1033* (2013.01); *A61M 2205/0216* (2013.01); *A61M 2207/00* (2013.01)

(58) Field of Classification Search
CPC .... A61M 2039/261; A61M 2039/0063; A61M 39/046
See application file for complete search history.

(56) References Cited

U.S. PATENT DOCUMENTS

| | | |
|---|---|---|
| 6,113,068 A | 9/2000 | Ryan |
| 8,157,784 B2 | 4/2012 | Rogers |
| 2003/0032940 A1 | 2/2003 | Dayle |
| 2004/0172006 A1* | 9/2004 | Bonaldo ............... A61M 39/26 604/523 |
| 2012/0157914 A1* | 6/2012 | Stroup ................. A61M 39/26 604/68 |
| 2014/0246616 A1 | 9/2014 | Fangrow |
| 2016/0361504 A1* | 12/2016 | Kim ..................... A61J 1/2096 |

FOREIGN PATENT DOCUMENTS

| | | |
|---|---|---|
| JP | H04-244169 A | 9/1992 |
| JP | 2002526179 A | 8/2002 |
| JP | 2012254142 A | 12/2012 |
| WO | 2016051759 A1 | 4/2016 |

OTHER PUBLICATIONS

Written Opinion (PCT/ISA/237) dated May 29, 2018, by the Japan Patent Office as the International Searching Authority for International Application No. PCT/JP2018/011872.

An English Translation of the International Search Report (Form PCT/ISA/210) and the Written Opinion of the International Searching Authority (Form PCT/ISA/237) dated May 29, 2018, by the Japanese Patent Office in corresponding International Application No. PCT/JP2018/011872. (5 pages).

Office Action (First Office Action) dated Apr. 6, 2021, by the State Intellectual Property Office of People's Republic of China in corresponding Chinese Patent Application No. 201880005695.9 and an English Translation of the Office Action. (11 pages).

* cited by examiner

MEDICAL DEVICE

CROSS-REFERENCES TO RELATED APPLICATIONS

This application is a continuation of International Application No. PCT/JP2018/011872 filed on Mar. 23, 2018, which claims priority to Japanese Application No. 2017-058832 filed on Mar. 24, 2017, the entire content of which is incorporated herein by reference.

FIELD OF THE DISCLOSURE

The present disclosure relates to a medical device.

BACKGROUND DISCUSSION

Conventionally, for use in medical devices used for infusion into a living body such as a human body, a medical connector or a syringe having a connector portion is known. The connector portion of such a medical device may be configured as a closable connector portion that can be closed by a valve body.

For example, U.S. Pat. No. 8,157,784 discloses a medical connector (medical device) including a closable male connector portion that can be closed by a valve body. When the male connector portion is connected with a female connector portion of another medical connector (another medical device), the valve body is pressed against an elastic valve of the female connector portion. Then, a spike provided on the male connector portion penetrates a contact portion between the valve body and the elastic valve, whereby the male connector portion is in fluid communication with the female connector portion. Such a configuration can reduce the risk of fluid leakage from the connector portions in forming fluid communication.

However, the conventional medical device (medical connector) as described in U.S. Pat. No. 8,157,784 has the risk of fluid leakage that may occur between the valve body and the elastic valve as a result of reduced adhesion between the valve body and the elastic valve, for example, after the connection between the connector portion (closable male connector portion) and another medical device (another medical connector) is released rather quickly.

SUMMARY

A medical device is disclosed, which has a connector portion which can help reduce the risk of fluid leakage.

A medical device according to an aspect of the present disclosure includes a connector portion. The connector portion includes a distal end, a proximal end, a central axial line, an inner cylinder connectable to another medical device having an elastic valve, a valve body against which the elastic valve is pressed from the distal end side due to connection of the inner cylinder and another medical device, and an outer cylinder disposed radially outside the inner cylinder, and the connector portion is configured to switch whether to provide fluid communication between the connector portion and another medical device by moving the inner cylinder in an axial direction along the central axial line with respect to the outer cylinder in a state where the inner cylinder is connected with another medical device. The connector portion further includes an anchor that suppresses movement of the valve body with respect to the inner cylinder toward the proximal end.

In accordance with an embodiment of the present disclosure, the anchor includes a protrusion, a stepped portion, or a rough surface portion formed on at least one of the inner cylinder and the valve body.

In accordance with an embodiment of the present disclosure, the inner cylinder includes a cylindrical retaining wall having an inner circumferential surface in contact with the valve body, and the anchor includes a protrusion, a stepped portion, or a rough surface portion formed on at least one of the retaining wall and the valve body.

In accordance with an embodiment of the present disclosure, the connector portion further includes a spike capable of penetrating the valve body.

In accordance with an embodiment of the present disclosure, the spike is disposed radially inward of the retaining wall, extends in the axial direction, and is integrally coupled with the outer cylinder, and a gap is formed in the axial direction between a distal end portion of the spike and the valve body when the inner cylinder is not connected with another medical device.

In accordance with another embodiment, a medical device is disclosed comprising: a connector portion, the connector portion including a distal end and a proximal end; an inner cylinder; a valve body; an outer cylinder disposed radially outside the inner cylinder, and wherein the connector portion is configured to provide fluid communication between the connector portion and another medical device by moving the inner cylinder in an axial direction along a central axial line of the connector portion with respect to the outer cylinder in a state where the inner cylinder is connected with another medical device; and an anchor configured to suppress movement of the valve body with respect to the inner cylinder toward the proximal end of the connector portion, and wherein the anchor includes a protrusion, a stepped portion, or a rough surface portion formed on at least one of the inner cylinder and the valve body.

In accordance with an embodiment, a medical device is disclosed comprising: a connector portion, the connector portion including a distal end and a proximal end; an inner cylinder connectable to another medical device having an elastic valve; a valve body against which the elastic valve is pressed from the distal end side due to connection of the inner cylinder and another medical device, the valve body has an apical tubular head having a slit through which a spike can penetrate, and a bellowed shape body that is elastically deformable in the axial direction; an outer cylinder disposed radially outside the inner cylinder, and wherein the connector portion is configured to provide fluid communication between the connector portion and another medical device by moving the inner cylinder in an axial direction along a central axial line of the connector portion with respect to the outer cylinder in a state where the inner cylinder is connected with another medical device; and an anchor configured to suppress movement of the valve body with respect to the inner cylinder toward the proximal end of the connector portion, and wherein the anchor includes a protrusion, a stepped portion, or a rough surface portion formed on at least one of the inner cylinder and the valve body.

According to the present disclosure, it is possible to provide a medical device provided with a connector portion capable of reducing the risk of fluid leakage.

DESCRIPTION OF EMBODIMENTS

Figure 1:
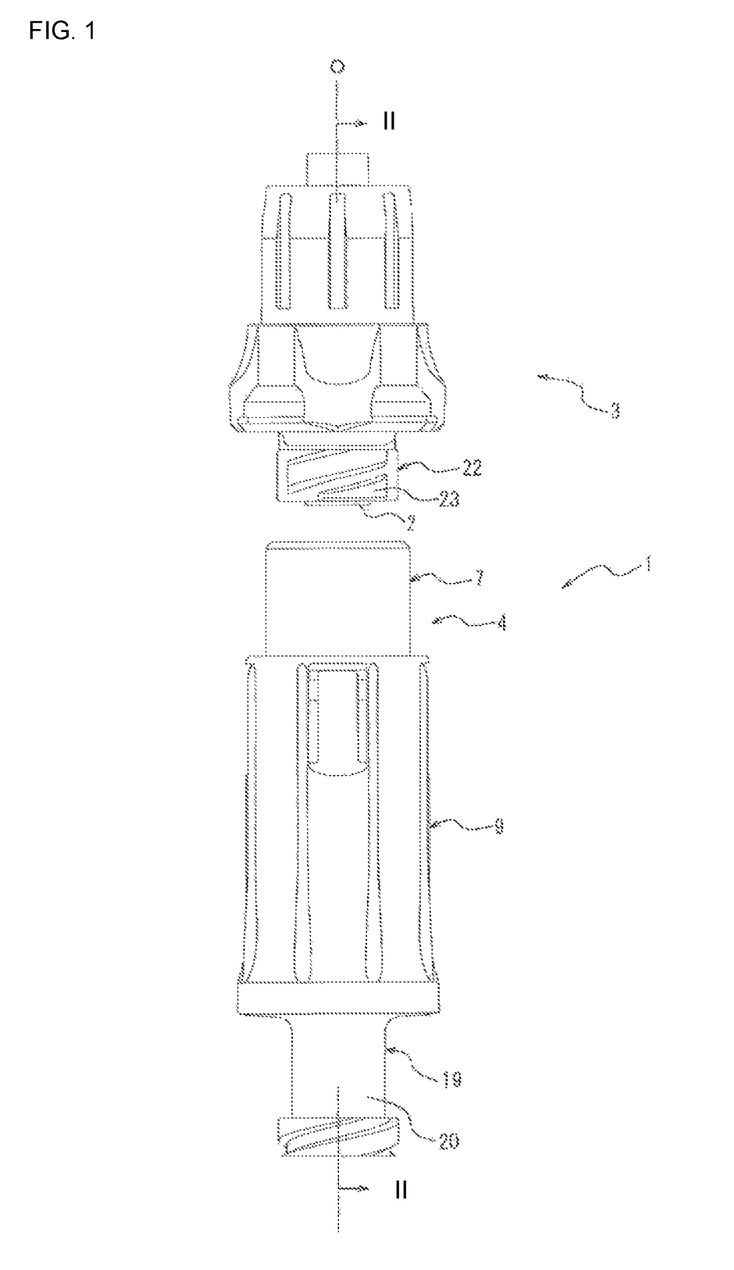
FIG. 1 is a side view illustrating a medical device according to one embodiment of the present disclosure together with another medical device.

Hereinafter, a medical device 1 according to one embodiment of the present disclosure will be illustrated and described in detail with reference to FIGS. 1 to 10. As illustrated in FIG. 1, the medical device 1 according to the present embodiment is configured as a medical connector used for infusion into a living body such as a human body, and includes a connector portion 4 that is capable of being in fluid communication with another medical device (a medical connector in this embodiment) 3 having an elastic valve 2. The medical device 1 may be a syringe or the like used for infusion to a living body such as a human body.

Figure 2:
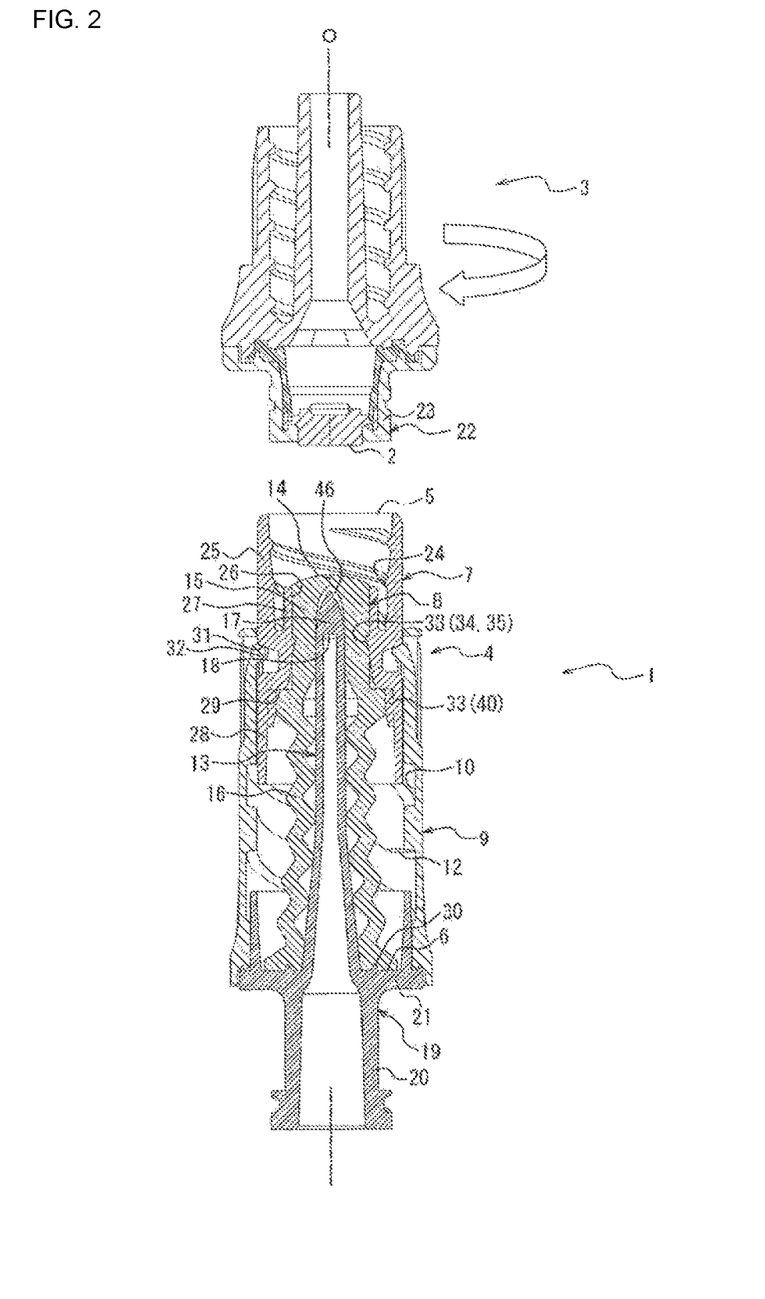
FIG. 2 is a cross-sectional view taken along line II-II in FIG. 1.
Figure 3:
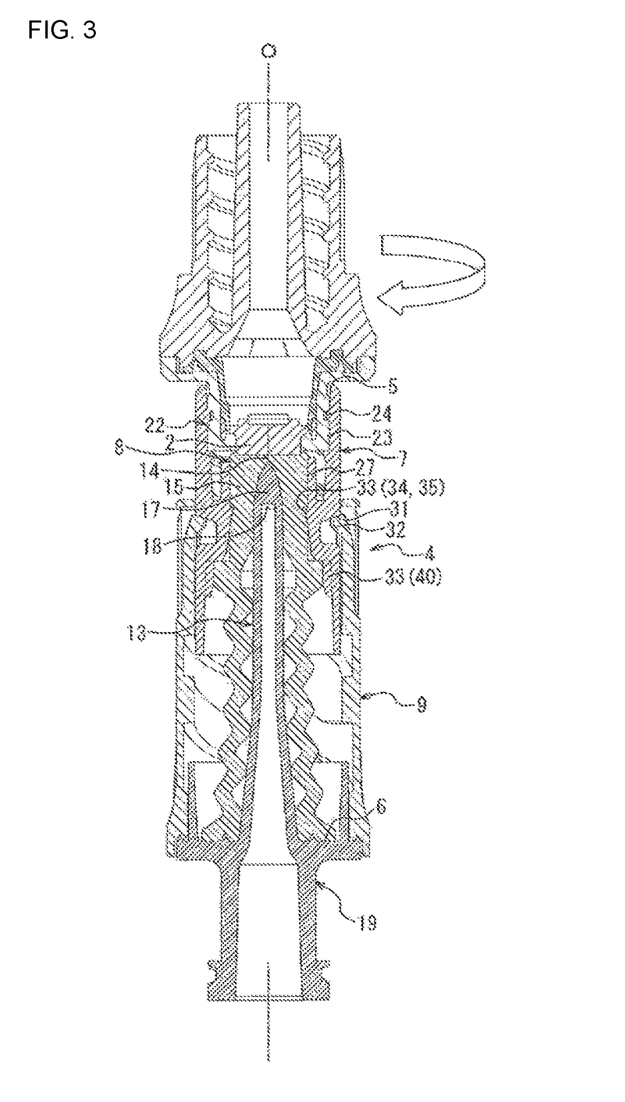
FIG. 3 is a cross-sectional view with reference to FIG. 2, illustrating a state where another medical device is connected with the inner cylinder of the medical device according to the embodiment of the present disclosure illustrated in FIG. 1.
Figure 4:
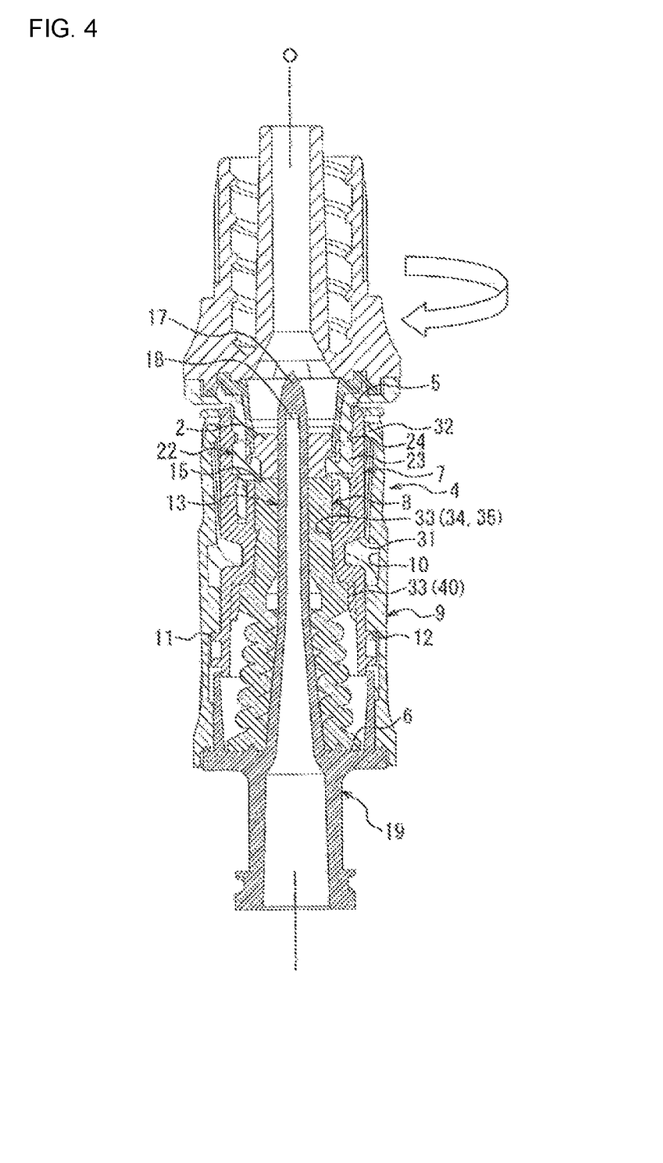
FIG. 4 is a cross-sectional view with reference to FIG. 2, illustrating a state where another medical device is in fluid communication with the medical device according to the embodiment of the present disclosure illustrated in FIG. 1.

As illustrated in FIG. 2, the connector portion 4 has a distal end 5, a proximal end 6, and a central axial line O. Furthermore, the connector portion 4 includes an inner cylinder 7 connectable to another medical device 3, a valve body 8 against which the elastic valve 2 is pressed from the distal end 5 side due to the connection of the inner cylinder 7 and another medical device 3, and an outer cylinder 9 disposed radially outside the inner cylinder 7. As illustrated in FIGS. 3 and 4, the connector portion 4 is configured to provide fluid communication between the connector portion 4 and to another medical device 3 by moving the inner cylinder 7 in the axial direction along the central axial line O with respect to the outer cylinder 9 in a state where the inner cylinder 7 is connected with another medical device 3. FIG. 3 illustrates a state where another medical device 3 is connected with the inner cylinder 7 of the medical device 1, and FIG. 4 illustrates a state where another medical device 3 is in fluid communication with the medical device 1.

Figure 5A:
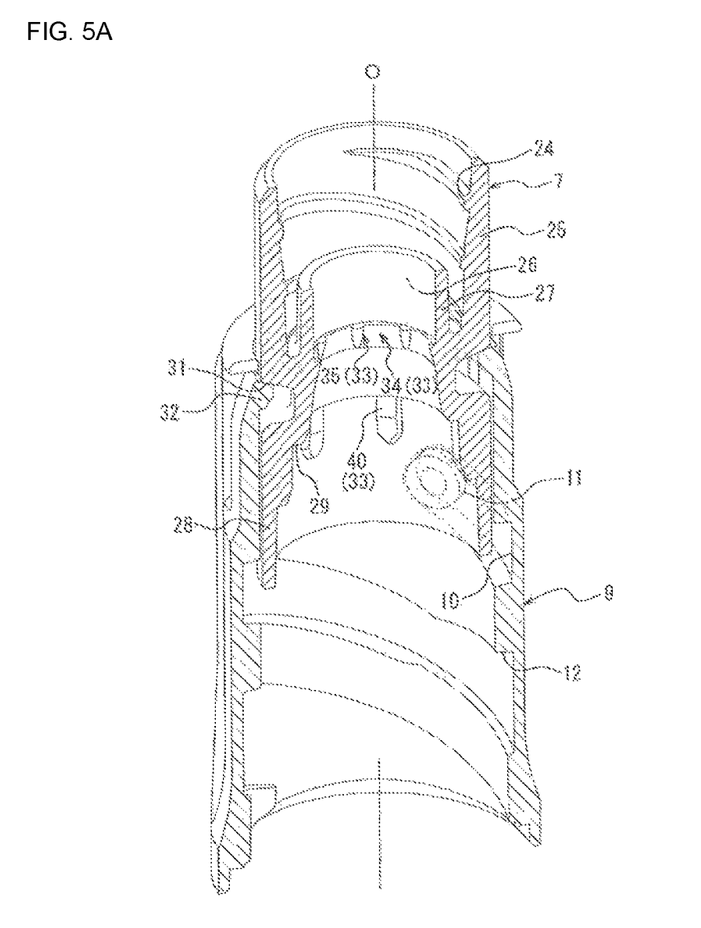
FIG. 5A is a cross-sectional perspective view taken along line II-II in FIG. 1, illustrating only the inner cylinder and the outer cylinder of the medical device according to the embodiment of the present disclosure.

As illustrated in FIG. 5A, in the present embodiment, the outer cylinder 9 has a thread groove 10, and the inner cylinder 7 has an engagement protrusion 11 guided in the thread groove 10. In the present embodiment, the thread groove 10 is configured as a double groove, and the engagement protrusion 11 is configured as two protrusions corresponding to the double groove. However, the thread groove 10 may be a single groove or triple or more groove. Furthermore, in the present embodiment, the engagement protrusion 11 is configured as a cylindrical protrusion, but the shape is not particularly limited as long as the protrusion is guided in the thread groove 10. In this example, the side wall provided on the distal end 5 side of the thread groove 10 is provided with a stop portion 12 where the lead angle decreases or disappears at the terminal end on the proximal end 6 side (terminal end of the movable range of the engagement protrusion 11). As illustrated in FIG. 4, in the fluid communication state, the engagement protrusion 11 is stopped at the stop portion 12, so that even when an external force in the direction in which the medical device 1 and another medical device 3 separate, that is, in a pulling direction is applied, the engagement protrusion 11 is not guided along the thread groove 10 toward the distal end 5 due to the external force in the pulling direction. Therefore, the inner cylinder 7 does not move toward the distal end 5 with respect to the outer cylinder 9 and the fluid communication is not released. The stop portion 12 may not necessarily be provided.

Figure 6A:
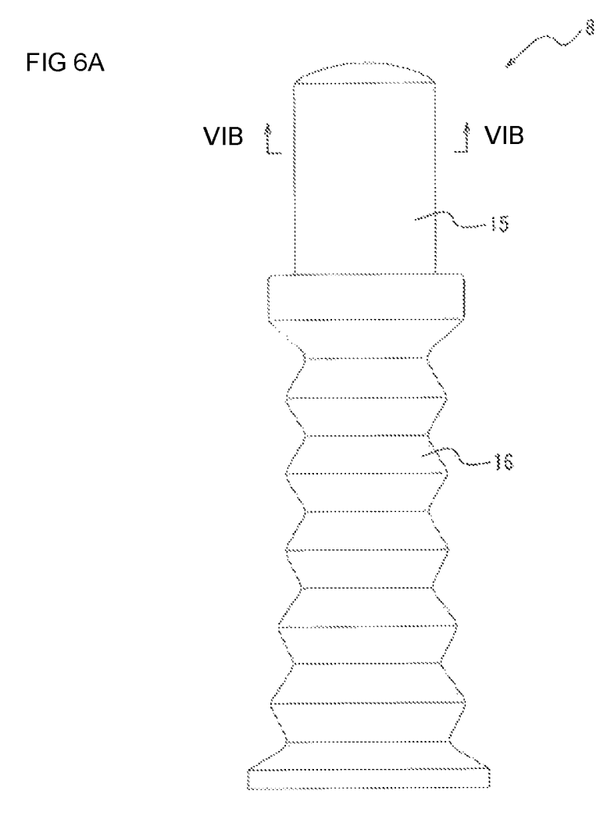
FIG. 6A is a side view illustrating a valve body in the medical device according to the embodiment of the present disclosure illustrated in FIG. 1.
Figure 6B:
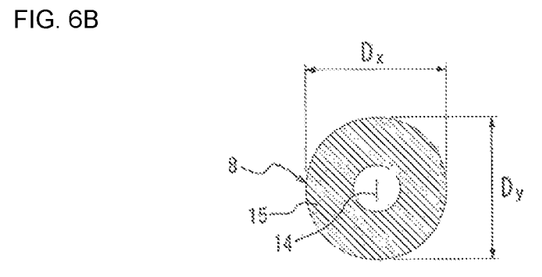
FIG. 6B is a cross-sectional view taken along line VIB-VIB in FIG. 6A.

In the present embodiment, as illustrated in FIG. 2, the connector portion 4 has a spike 13 that can penetrate the valve body 8. As illustrated in FIGS. 6A and 6B, the valve body 8 has an apical tubular head 15 having a slit 14 through which the spike 13 (see FIG. 2) can penetrate, and a body 16 that is elastically deformable in the axial direction. In accordance with an exemplary embodiment, the body 16 is stretchable by being formed in a bellows shape. In the present embodiment, the head 15 and the body 16 of the valve body 8 can be integrally formed, but may be separately formed. In accordance with an exemplary embodiment, instead of the body 16, for example, a coil spring may be used.

Figure 7:
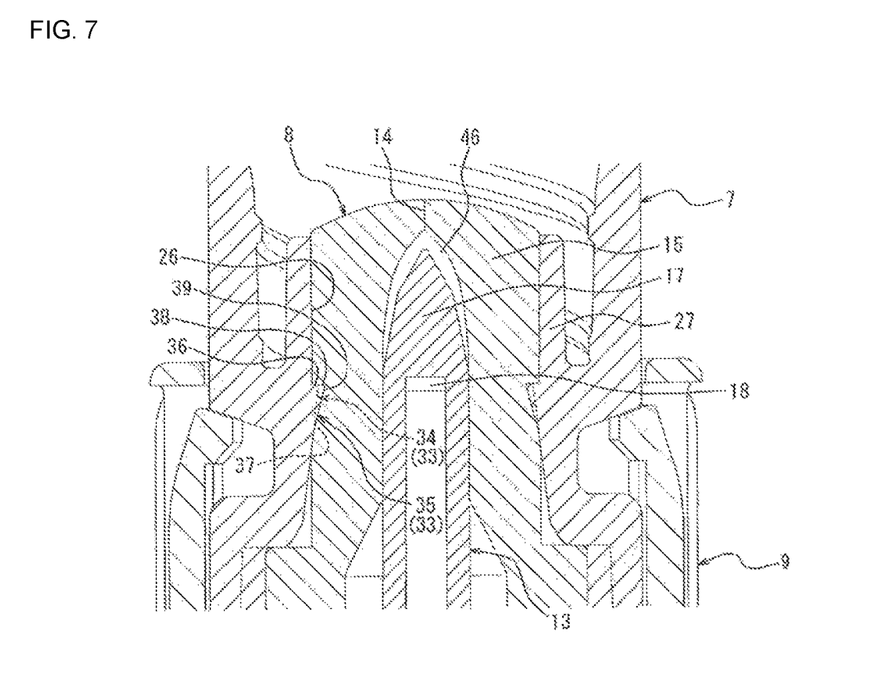
FIG. 7 is a partial enlarged view of FIG. 2.

As illustrated in FIG. 7, the spike 13 has a tubular shape which extends in the axial direction and which is closed by the distal end portion 17, and the distal end portion 17 is formed in a sharp pointed shape. In addition, a communication hole 18 that penetrates the spike 13 is formed on the side surface of the distal end portion 17. Therefore, when the spike 13 penetrates the head portion 15 of the valve body 8, the spike 13 can form in the valve body 8, a flow path for a fluid such as a chemical solution (see FIG. 4). As illustrated in FIG. 2, in the present embodiment, the spike 13 constitutes a part of a flow path forming member 19. In accordance with an exemplary embodiment, the flow path forming member 19 has a female connector portion 20 coupled to the proximal end portion of the spike 13 and a flange 21 integrally coupled to the proximal end portion of the outer cylinder 9. Thus, in the present embodiment, the spike 13 is integrally coupled with the outer cylinder 9.

As illustrated in FIG. 2, another medical device 3 has a closable female connector portion 22 that can be closed by the elastic valve 2. The inner cylinder 7 has a cylindrical connection cylinder 25 having on the inner circumferential surface a thread portion 24 to be engaged with a thread portion 23 provided on the outer circumferential surface of the female connector portion 22 of another medical device 3. Furthermore, the inner cylinder 7 has a tubular (in this example, cylindrical) retaining wall 27 having an inner circumferential surface 26 coupled to the proximal end portion of the connection cylinder 25 and brought in contact with the head portion 15 of the valve body 8. The top surface (distal end surface) of the valve body 8 protrudes from the distal end portion of the retaining wall 27 to the distal end side in order to improve adhesion with the elastic valve 2 in the state where the inner cylinder 7 and another medical device 3 are connected with each other. The lower end portion (proximal end portion) of the retaining wall 27 is coupled to the distal end portion of a cylindrical engagement cylinder 28 having the engagement protrusion 11 (see FIG. 5A) on the outer circumferential surface. An annular stepped portion 29 extending in the radial direction is formed at the joint of the retaining wall 27 and the engagement cylinder 28. The distal end portion of the body portion 16 of the valve body 8 is in contact with the annular stepped portion 29, and the proximal end portion of the body portion 16 is in contact with the flange 21 of the flow path forming member 19. As described above, in the present embodiment, the inner cylinder 7 is biased toward the distal end 5 by the body portion 16 of the valve body 8. The flange 21 is provided with an annular seal projection 30 for enhancing the sealability with the proximal end portion of the body portion 16. Furthermore, the spike 13 is disposed radially inward of the retaining wall 27.

In accordance with an exemplary embodiment, between the connection cylinder 25 and the engagement cylinder 28, an engagement recess 31 (formed in an annular shape in this embodiment) is provided as an engagement portion engageable with the outer cylinder 9, and the outer cylinder 9 is provided with engagement claws 32 (in this example, for example, four engagement claws are arranged at equal intervals in the circumferential direction) that can be locked to the engagement recess 31.

In accordance with an exemplary embodiment, when another medical device 3 is screwed into the inner cylinder 7 as illustrated in FIG. 3 in the state where the inner cylinder 7 is engaged with the outer cylinder 9, the valve body 8 is pressed against the elastic valve 2, and another medical device 3 is connected with the inner cylinder 7. Next, when another medical device 3 is rotated in the same direction as when screwing another medical device 3 into the inner cylinder 7, the engagement between the outer cylinder 9 and the inner cylinder 7 is released as the engagement claws 32 separate from the engagement recess 31. In accordance with an exemplary embodiment, the engagement protrusion 11 of the inner cylinder 7 is guided along the thread groove 10 of the outer cylinder 9 toward the proximal end 6, and the head portion 15 of the valve body 8 and the elastic valve 2 are moved together with the inner cylinder 7 toward the proximal end 6. The head portion 15 and the elastic valve 2 are then penetrated by the spike 13, and as illustrated in FIG. 4, the connector portion 4 and another medical device 3 are in fluid communication. In accordance with an exemplary embodiment, to separate the medical device 1 from another medical device 3, it suffices that another medical device 3 is rotated in the opposite direction to the direction described above with respect to the medical device 1.

Figure 5B:
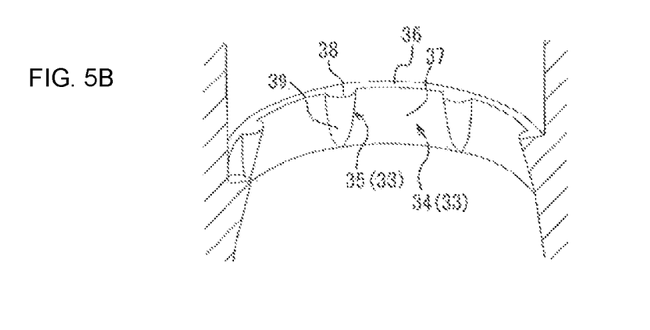
FIG. 5B is a partially enlarged view of FIG. 5A.

In the present embodiment, as illustrated in FIGS. 5B and 7, anchors 33 are integrally formed on the inner circumferential surface 26 of the retaining wall 27. The anchors 33 are configured to suppress movement of the valve body 8 relative to the inner cylinder 7 toward the proximal end 6. In this embodiment, the anchors 33 include an annular protrusion 34 formed over the entire circumference of the inner circumferential surface 26 of the retaining wall 27, and a plurality of (in this embodiment, for example, eight) small protrusions 35 arranged on the annular protrusion 34 at intervals (in this example, equal intervals) in the circumferential direction. In accordance with an exemplary embodiment, the annular protrusion 34 has an annular end surface 36 disposed on the distal end 4 side and protruding radially inward, and an annular inclined surface 37 having a radially inward protrusion width that gradually increases from the proximal end 6 side end toward the annular end surface 36. In accordance with an exemplary embodiment, the plurality of small protrusions 35 is disposed on the inclined surface 37. In accordance with an exemplary embodiment, each small protrusion 35 has a semicircular end surface 38 disposed on the distal end 4 side and protruding radially inward, and an inclined surface 39 having a radially inward protrusion width that gradually increases from the proximal end 6 side end toward the annular end surface 36. Thus, the anchors 33 include the annular protrusion 34 and the small protrusions 35 formed in the inner circumferential surface 26 of the retaining wall 27 in this embodiment.

In accordance with an exemplary embodiment, since the annular inclined surface 37 and the inclined surface 39 are inclined as described above, not only the movement of the valve body 8 relative to the inner cylinder 7 toward the proximal end 6 can be suppressed, but also the valve body 8 can be rather easily incorporated into the inner cylinder 7 in the manufacturing process of the medical device 1. Furthermore, when the anchors 33 include protrusions formed on the inner circumferential surface 26 of the holding retaining 27 as described above, the anchors 33 may include a plurality of or a single small protrusion 35 alone without providing the annular protrusion 34.

According to the present embodiment, since the connector portion 4 has the anchors 33, adhesion can be improved between the valve body 8 and the elastic valve 2 in the state where the inner cylinder 7 and another medical device 3 are connected with each other as illustrated in FIG. 3. As a result, the risk of fluid leakage from the connector portion 4 can be reduced. In particular, since the anchors 33 are provided on the retaining wall 27 in this embodiment, the movement of the valve body 8 can be suppressed at a portion relatively close to the top surface (distal end surface) of the valve body 8 pressed by the elastic valve 2, and thus the adhesion between the valve body 8 and the elastic valve 2 can be effectively improved.

As illustrated in FIG. 2, in this embodiment, the anchors 33 are also provided on the inner circumferential surface of the engagement cylinder 28. The anchors 33 provided on the engagement cylinder 28 include a plurality of (in this embodiment, for example, six) large protrusions 40 disposed at intervals (in this example, for example, at equal intervals) in the circumferential direction at the upper end portion (distal end portion) on the inner circumferential surface of the engagement cylinder 28. The large protrusions 40 are configured to coming into contact with the distal end portion of the body portion 16 of the valve body 8, thereby, with the frictional force of the distal end portion of the body portion 16 of the valve body 8, suppressing movement of the valve body 8 relative to the inner cylinder 7 toward the proximal end 6. In accordance with an exemplary embodiment, the anchors 33 may be provided on only one of the retaining wall 27 and the engagement cylinder 28, or may be provided alternatively or additionally at another portion. When providing the anchors 33 in the inner cylinder 7, in accordance with an exemplary embodiment, the valve body 8 may be provided with recesses for receiving the anchors 33 as appropriate.

Figure 8:
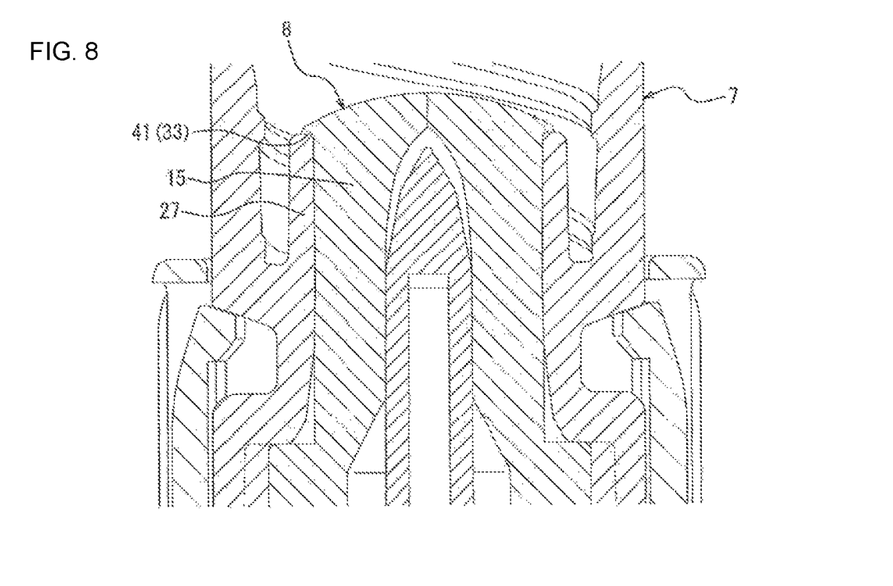
FIG. 8 is a cross-sectional view with reference to FIG. 7, illustrating a modification of the medical device according to one embodiment of the present disclosure illustrated in FIG. 1.

In accordance with an exemplary embodiment, the anchors 33 may be provided to the valve body 8, as illustrated in FIG. 8. In the modification illustrated in FIG. 8, an annular stepped portion 41 facing downward is provided at the distal end portion on the outer circumferential surface of the head portion 15 of the valve body 8. The annular stepped portion 41 is engaged with the distal end surface of the retaining wall 27. In this manner, by providing the anchors 33 including a stepped portion to the valve body 8, it is possible to suppress movement of the valve body 8 with respect to the inner cylinder 7 toward the proximal end 6. In accordance with an exemplary embodiment, instead of or in addition to the stepped portion, the valve body 8 may be provided with an anchor 33 including a protrusion. In this case, the inner cylinder 7 may be provided with a recess for receiving this anchor 33.

Figure 9:
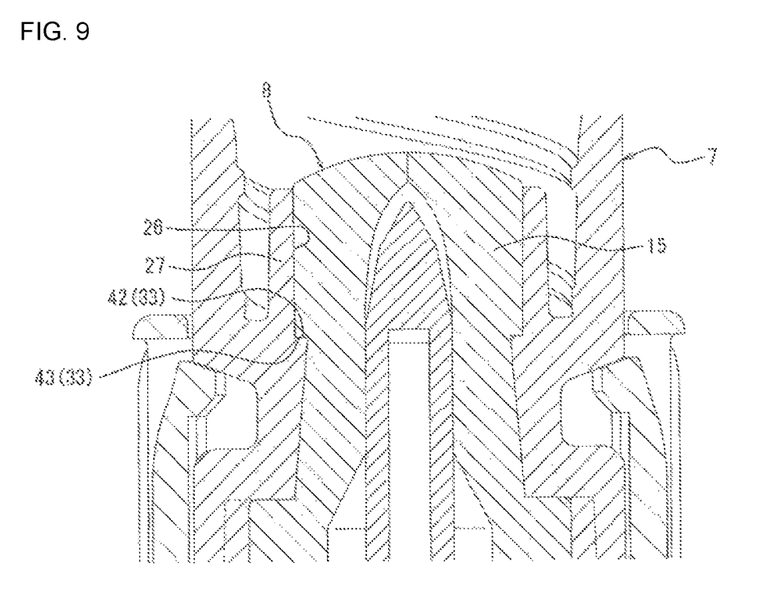
FIG. 9 is a cross-sectional view with reference to FIG. 7, illustrating another modification of the medical device according to one embodiment of the present disclosure illustrated in FIG. 1.

In accordance with an exemplary embodiment, the anchors 33 may include stepped portions provided to both the inner cylinder 7 and the valve body 8 as illustrated in FIG. 9, for example. In the modification illustrated in FIG. 9, the anchors 33 include an annular stepped portion 42 facing upward and being formed on the inner circumferential surface 26 of the retaining wall 27 over the entire circumference of inner circumferential surface 26 of the retaining wall 27, and an annular stepped portion 43 facing downward and being formed on the outer circumferential surface of the head portion 15 of the valve body 8 over the entire circumference of inner circumferential surface 26 of the retaining wall 27. The annular stepped portion 42 of the retaining wall 27 engages with the annular stepped portion 43 of the valve body 8. In this manner, by providing the anchors 33 including stepped portions to both the inner cylinder 7 and the valve body 8, it is possible to help suppress movement of the valve body 8 with respect to the inner cylinder 7 toward the proximal end 6.

Figure 10:
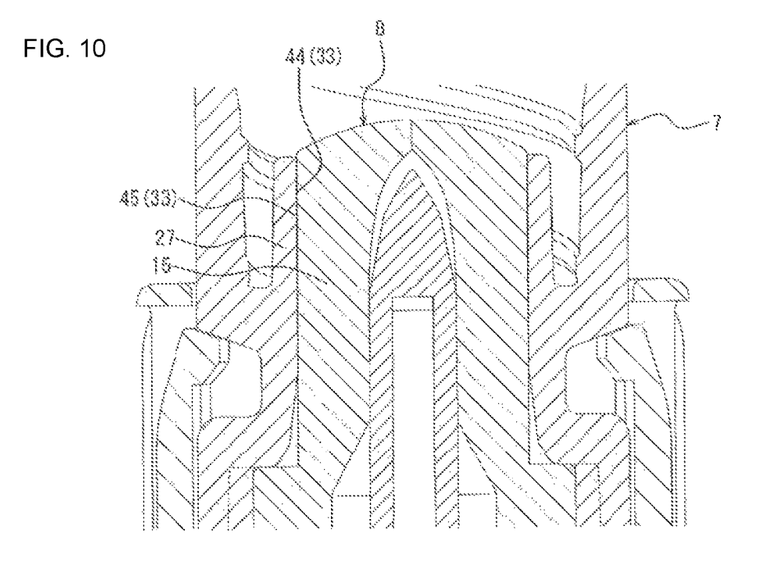
FIG. 10 is a cross-sectional view with reference to FIG. 7, illustrating a further modification of the medical device according to one embodiment of the present disclosure illustrated in FIG. 1.

In accordance with an exemplary embodiment, as illustrated in FIG. 10, for example, the anchors 33 may include a rough surface 44 formed on the inner cylinder 7 and a rough surface 45 formed on the valve body 8. In this manner, by bringing the inner cylinder 7 and the valve body 8 into contact with each other through the rough surfaces 44, 45, frictional resistance between the inner cylinder 7 and the valve body 8 is increased, and it is possible to help suppress movement of the valve body 8 with respect to the inner cylinder 7 toward the proximal end 6. In accordance with an exemplary embodiment, one of the rough surface 44 of the inner cylinder 7 and the rough surface 45 of the valve body 8 is not necessarily provided. The rough surface 44 of the inner cylinder 7 is preferably formed on the retaining wall 27 as illustrated in FIG. 10, and the rough surface 45 of the valve body 8 is preferably formed on the head portion 15 as illustrated in FIG. 10. In accordance with an exemplary embodiment, such rough surface portions (rough surfaces 44, 45) may be provided in combination with the above-mentioned protrusions and/or stepped portions.

Furthermore, in the present embodiment, as illustrated in FIGS. 2 and 7, when the inner cylinder 7 is not connected with another medical device 3, a gap 46 can be formed in the axial direction between the distal end portion 17 of the spike 13 and the valve body 8. Therefore, as illustrated in FIG. 3, even if the elastic valve 2 is pressed from the distal end 5 side to the valve body 8 by the connection between the inner cylinder 7 and another medical device 3 and thus a portion of the valve body 8 that is closer to the distal end side with respect to the anchors 33 (the annular protrusion 34, the small protrusion 35) can be compressed, the gap 46 in the axial direction functions as a play (i.e., allowing slight movement of the distal end portion 17 of the spike 13 without engaging the valve body 8) and can help suppress opening of the slit 14 by the distal end portion 17 of the spike 13. Therefore, in this example, providing the gap 46 also helps reduce the risk of fluid leakage. In accordance with an exemplary embodiment, such a gap 46 is not necessarily provided.

Furthermore, in the present embodiment, the slit 14 has a straight linear shape when viewed from the distal end 5 side. As illustrated in FIG. 6B, the head portion 15 of the valve body 8 has an elliptic cylindrical shape in which the outer diameter $D_x$ in the direction orthogonal to the slit 14 is larger than the outer diameter $D_y$ in the direction along the slit 14. The inner circumferential surface 26 of the retaining wall 27 has a cylindrical shape. Thus, the head portion 15 of the valve body 8 is compressed by the inner circumferential surface 26 of the retaining wall 27 in the direction in which the slit 14 is closed. Therefore, in this embodiment, the valve body 8 is compressed in the direction in which the slit 14 is closed, and the risk of fluid leakage is reduced also by enhancing the closedness (i.e., a force of the opposing edges of the slit 14 towards one another) of the slit 14. The valve body 8 is not necessarily compressed.

Moreover, although the outer cylinder 9, the inner cylinder 7, and the flow path forming member 19 can each be formed by injection molding of a synthetic resin material, for example, the material, the molding method, and the like are not specifically limited. In accordance with an exemplary embodiment, although the valve body 8 can be formed by injection molding of an elastic material, such as rubber or a thermoplastic elastomer, for example, the material, the molding method, and the like are not specifically limited. Furthermore, the outer cylinder 9, the inner cylinder 7, the flow path forming member 19, and the valve body 8, each of which is formed of a single component in the present embodiment, may include a plurality of components.

While one embodiment of the present disclosure has been described, the aforementioned only shows an example of embodiments of the present disclosure, and it should be understood that various changes can be made unless they depart from the spirit and scope of the present disclosure.

The detailed description above describes to a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
    a connector portion, the connector portion including a distal end, a proximal end, and a central axial line;
    an inner cylinder connectable to another medical device having an elastic valve;
    a valve body against which the elastic valve is pressed from the distal end side due to connection of the inner cylinder and the another medical device;
    an outer cylinder disposed radially outside the inner cylinder, and wherein the connector portion is configured to provide fluid communication between the connector portion and the another medical device by moving the inner cylinder in an axial direction along the central axial line with respect to the outer cylinder in a state where the inner cylinder is connected with the another medical device;

an anchor configured to suppress movement of the valve body with respect to the inner cylinder toward the proximal end of the connector portion;

the inner cylinder including a cylindrical connection cylinder having an inner circumferential surface configured to be engaged with an outer circumferential surface of a female connector portion of the another medical device;

the inner cylinder including a tubular retaining wall, the tubular retaining wall having an inner circumferential surface in contact with the valve body and coupled to a proximal end portion of the cylindrical connection cylinder; and wherein a proximal end portion of the retaining wall is coupled to a distal end portion of a cylindrical engagement cylinder, and the anchor is a plurality of anchors provided on an inner circumferential surface of the engagement cylinder.

2. The medical device according to claim 1, wherein each of the plurality of anchors includes a protrusion, a stepped portion, or a rough surface portion formed on the inner circumferential surface of the engagement cylinder.

3. The medical device according to claim 1, wherein the connector portion further includes a spike configured to penetrate the valve body.

4. The medical device according to claim 3, wherein the spike is disposed radially inward of the retaining wall, extends in the axial direction, and is integrally coupled with the outer cylinder.

5. The medical device according to claim 4, further comprising:

a gap in the axial direction between a distal end portion of the spike and the valve body when the inner cylinder is not connected with the another medical device.

6. The medical device according to claim 1, wherein the inner circumferential surface of the inner cylinder includes a thread portion configured to be engaged with a thread portion on the outer circumferential surface of the female connector portion of the another medical device.

7. The medical device according to claim 1, wherein an annular protrusion is arranged on the inner circumferential surface of the retaining wall of the inner cylinder.

8. The medical device according to claim 7, wherein the annular protrusion is integrally formed on the inner circumferential surface of the retaining wall.

9. The medical device according to claim 7, wherein a plurality of protrusions are arranged on the annular protrusion at equal intervals in a circumferential direction.

10. The medical device according to claim 9, wherein the annular protrusion has an annular end surface disposed on a distal end side and protruding radially inward, and an annular inclined surface having a radially inward protrusion width that gradually increases from a proximal end side end toward an annular end surface.

11. The medical device according to claim 10, wherein the plurality of protrusions are disposed on the inclined surface, and each of the plurality of protrusions has a semicircular end surface disposed on a distal end side and protruding radially inward, and an inclined surface having a radially inward protrusion width that gradually increases from the proximal end side end toward the annular end surface.

12. The medical device according to claim 1, wherein the valve body has an apical tubular head having a slit through which a spike can penetrate, and a body that is elastically deformable in the axial direction.

13. A medical device comprising:

a connector portion, the connector portion including a distal end and a proximal end;

an inner cylinder;

a valve body;

an outer cylinder disposed radially outside the inner cylinder, and wherein the connector portion is configured to provide fluid communication between the connector portion and another medical device by moving the inner cylinder in an axial direction along a central axial line of the connector portion with respect to the outer cylinder in a state where the inner cylinder is connected with another medical device;

a plurality of anchors configured to suppress movement of the valve body with respect to the inner cylinder toward the proximal end of the connector portion, and wherein each of the plurality of anchors includes a protrusion, a stepped portion, or a rough surface portion;

the inner cylinder including a cylindrical connection cylinder having an inner circumferential surface configured to be engaged with an outer circumferential surface of a female connector portion of the another medical device;

the inner cylinder including a tubular retaining wall, the tubular retaining wall having an inner circumferential surface in contact with the valve body and coupled to a proximal end portion of the cylindrical connection cylinder; and wherein a proximal end portion of the retaining wall is coupled to a distal end portion of a cylindrical engagement cylinder, and the plurality of anchors are provided on an inner circumferential surface of the engagement cylinder.

14. The medical device according to claim 13, wherein the connector portion further includes a spike configured to penetrate the valve body, the spike being disposed radially inward of the retaining wall and extending in the axial direction.

15. A medical device comprising:

a connector portion, the connector portion including a distal end and a proximal end;

an inner cylinder connectable to another medical device having an elastic valve;

a valve body against which the elastic valve is pressed from the distal end side due to connection of the inner cylinder and another medical device, the valve body has an apical tubular head having a slit through which a spike can penetrate, and a bellowed shape body that is elastically deformable in an axial direction;

an outer cylinder disposed radially outside the inner cylinder, and wherein the connector portion is configured to provide fluid communication between the connector portion and another medical device by moving the inner cylinder in the axial direction along a central axial line of the connector portion with respect to the outer cylinder in a state where the inner cylinder is connected with another medical device;

a plurality of anchors configured to suppress movement of the valve body with respect to the inner cylinder toward the proximal end of the connector portion, and wherein each of the plurality of anchors includes a protrusion, a stepped portion, or a rough surface portion;

the inner cylinder including a cylindrical connection cylinder having an inner circumferential surface configured to be engaged with an outer circumferential surface of a female connector portion of the another medical device;

the inner cylinder including a tubular retaining wall, the tubular retaining wall having an inner circumferential surface in contact with the valve body and coupled to a proximal end portion of the cylindrical connection cylinder; and wherein a proximal end portion of the retaining wall is coupled to a distal end portion of a cylindrical engagement cylinder, and the plurality of anchors are provided on an inner circumferential surface of the engagement cylinder.

* * * * *